United States Patent [19]

Wiechert et al.

[11] 4,012,510

[45] Mar. 15, 1977

[54] NOVEL METHYLENE STEROIDS

[75] Inventors: Rudolf Wiechert; Klaus Kieslich; Henning Koch, all of Berlin, Germany

[73] Assignee: Schering Aktiengesellschaft, Berlin & Bergkamen, Germany

[22] Filed: Nov. 10, 1975

[21] Appl. No.: 630,627

[30] Foreign Application Priority Data

Nov. 11, 1974 Germany ............................. 2453823

[52] U.S. Cl. ........................... 424/243; 260/397.45; 260/397.47; 260/397.3; 260/397.4; 195/51 S

[51] Int. Cl.[2] .......................................... A61K 31/56

[58] Field of Search ................... 260/397.3, 397.45; 424/243; /Machine Searched Steroids

[56] References Cited

UNITED STATES PATENTS 3,700,702  10/1972  Furst et al. .................... 260/397.45

Primary Examiner—Elbert L. Roberts
Attorney, Agent, or Firm—Millen & White

[57] ABSTRACT

Methylene steroids of the formula

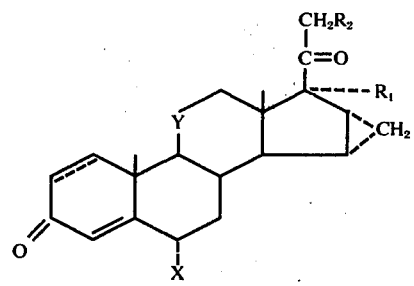

wherein X is H, F or $CH_3$; Y is hydroxymethylene, alkanoyloxymethylene or carbonyl; $R_1$ is H, OH or alkanoyloxy; and $R_2$ is H, OH or esterified OH, possess topical anti-inflammatory activity.

24 Claims, No Drawings

NOVEL METHYLENE STEROIDS

BACKGROUND OF THE INVENTION

This invention relates to novel, pharmacologically active methylene steroids, to processes for the preparation and use thereof, and to pharmaceutical preparations comprising them.

SUMMARY OF THE INVENTION

In a composition aspect, this invention relates to novel methylene steroids of the general Formula I

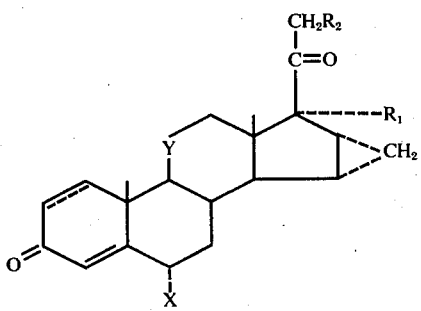

wherein

X is a hydrogen atom, a fluorine atom, or methyl;

Y is hydroxymethylene, alkanoyloxymethylene or carbonyl;

$R_1$ is a hydrogen atom, hydroxy, or alkanoyloxy; and $R_2$ is a hydrogen atom, hydroxy or a hydroxy group esterified with a physiologically acceptable acid.

In another composition aspect, this invention relates to pharmaceutical compositions comprising a novel methylene compound of this invention, more particularly, pharmaceutical compositions comprising an anti-inflammatorily effective concentration of one or two methylene compounds of this invention in admixture with a physiologically acceptable carrier adapted for topical administration.

In process aspects, this invention relates to processes for the production and for the use in treatment of topical inflammatory conditions of the novel methylene compounds of this invention.

DETAILED DISCUSSION

In the compounds of Formula I, the linkage represents a single bond or a double bond.

Examples of esterified $R_2$ hydroxy groups are esters of the physiologically acceptable organic carboxylic acids conventionally employed for the esterification of steroid alcohols. Preferred acyl groups are those wherein $R_2$ is alkanoyloxy of 1–8 carbon atoms, e.g., wherein alkanoyl is the acyl radical of formic, acetic, propionic, butyric, isobutyric, valeric, isovaleric, caproic, caprylic and enanthylic acid. Although alkanoyl of 1–8 carbon atoms are preferred, contemplated equivalents are steroids of Formula I wherein $R_2$ is acyloxy in which acyl is the acyl group of another organic acid, e.g., a carboxylic acid of up to 15 carbon atoms, especially an aliphatic carboxylic acid, e.g., an alkanoic acid of 9–18 carbon atoms, which can be unsaturated, branched, polybasic, or substituted in the usual manner, for example, by hydroxy or halogen atoms; a cycloaliphatic, aromatic and mixed aromatic-aliphatic (alkaryl and aralkyl) acid, which can likewise be substituted in the usual manner. Examples of such equivalent acids are pelargonic, capric, undecyclic, oleic, palmitic, dichloroacetic acid, β-cyclopentylpropionic acid, phenylpropionic acid, phenylacetic acid, phenoxyacetic acid, succinic acid, benzoic acid; others being acids containing 1–18 carbon atoms, preferably 2–12 carbon atoms, including an aliphatic acid containing 1–18 carbon atoms, preferably 1–6 carbon atoms, e.g., a cyclic acid, preferably a cycloaliphatic acid, containing, e.g., 4–18 carbon atoms, e.g., cyclopropylcarboxylic, cyclobutylcarboxylic, cyclopentylcarboxylic, cyclopentylacetic, β-cyclopentylpropionic, cyclohexylcarboxylic, cyclohexylacetic and β-cyclohexylpropionic acid; a carbocyclic aryl or alkaryl acid, e.g., containing 7–18 carbon atoms, and 1 to 5, preferably 1 or 2 rings, e.g., benzoic, 2-, 2-, or 4-methylbenzoic, 2,3-, 2,4-, 2,5-, 2,6-, 3,4-, and 3,5-dimethylbenzoic, ethylbenzoic, 2,3,6-trimethylbenzoic and 3-methyl-α-naphthoic acid; an aralkyl acid, e.g., containing 8 to 18 carbon atoms, e.g., phenylacetic, β-phenylpropionic, a polybasic acid, e.g., containing 2–18 carbon atoms and 1 to 5 hydroxy groups, e.g., glycolic, lactic, citric, tartaric, d-maleic, d-glyceric, and salicylic acid; and the corresponding acids containing one, two or more of simple substituents, e.g., halo, amino, alkoxy, acyloxy, etc., in the molecule, e.g., hydroxyacetic, monochloroacetic and dichloroacetic, trichloroacetic, dimethylaminoacetic, trimethylaminoacetic, diethylaminoacetic, piperidinoacetic, nicotinic, ω-carboxypropionic, and ω-carboxypentanoic acids.

To produce water-soluble esters, the 21-acyloxy esters bearing a basic nitrogen atom in the acyl radical can be converted into the corresponding physiologically acceptable acid addition salts thereof, e.g., hydrochlorides, hydrobromides, sulfates, phosphates, oxalates, tartrates and maleates. The 21-monoesters of dicarboxylic acid as well as the sulfuric acid and phosphoric acid esters can also be converted into a base salt thereof, e.g., amine or metal salts, preferably alkali metal salts, e.g., sodium and potassium salts, to increase their water solubility.

Examples of esterified hydroxy groups in the 11- or 17-position are alkanoyloxy, preferably of 1–8 carbon atoms, e.g., acetoxy, propionyloxy, butyryloxy, pentanoyloxy and/or hexanoyloxy. Contemplated as equivalents, to the extent they can be prepared, are alkanoyloxy of more than 8 carbon atoms, e.g., 8–16 carbon atoms, and other acyloxy groups, e.g., those discussed hereinabove as esterified 21-hydroxy groups.

Examples of contemplated classes of compounds within the scope of Formula I are those wherein:

a. $R_2$ is H;

b. $R_2$ is OH;

c. $R_2$ is $-OSO_3H$ or $-OPO(OH)_2$ and physiologically acceptable salts thereof with bases, e.g., ammonia, amines, preferably secondary and tertiary amines, e.g., diethylamine, triethylamine, and with metals, preferably alkali-metals, e.g., Na or K;

d. $R_2$ is alkanoyloxy of 1–8 carbon atoms, preferably acetoxy;

e. Y is β-hydroxymethylene, including each of (a), (b), (c), and (d);

f. Y is α-hydroxymethylene or α-alkanoyloxymethylene, including each of (a), (b), (c), and (d);

g. Y is carbonyl, including each of (a), (b), (c), and (d);

h. $R_1$ is OH, including each of (a), (b), (c), (d), (e), (f) and (g);

i. R₁ is alkanoyloxy, including each of (a), (b), (c), (d), (e), (f), and (g);

j. R₁ is H, including each of (a), (b), (c), (d), (e), (f) and (g);

k. X is H, including each of (a), (b), (c), (d), (e), (f), (g), (h), (i) and (j);

l. X is F, including each of (a), (b), (c), (d), (e), (f), (g), (h), (i) and (j); and m. X is CH₃, including each of (a), (b), (c), (d), (e), (f), (g), (h), (i) and (j), e.g., the 6α-methyl compounds corresponding to each of the 6α-hydrogen compounds of the examples hereinafter.

In a process aspect, this invention relates to a process for the preparation of the novel methylene steroids of Formula I wherein:

a. a compound of general Formula II

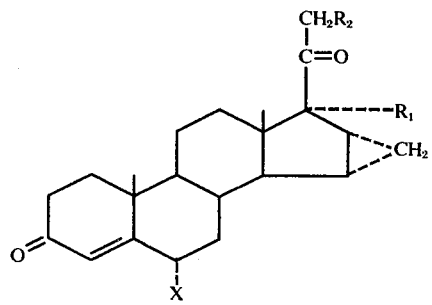

wherein X, R₁, and R₂ have the values given for Formula I, is fermented with a culture of a microorganism capable of 11-hydroxylation, and, optionally, additionally dehydrogenated in the 1,2-position; and, optionally thereafter, a hydroxy group present in the 11-position is oxidized to a carbonyl group and/or any ester groups present are saponified, or any free hydroxy groups present are esterified; or b. for the preparation of 15α,16α-methylene-Δ¹,⁴-corticoids of general Formula I, a compound of general Formula

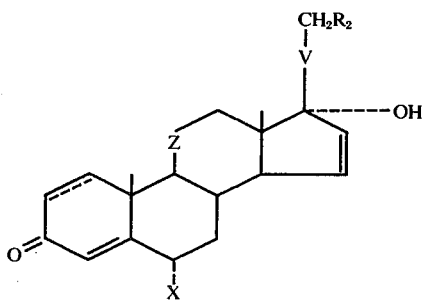

wherein ====
and X have the values given for Formula I,
Z and V are optionally esterified or etherified hydroxymethylene or optionally ketalized carbonyl, and
R₃ is a hydrogen atom or an optionally esterified or etherified hydroxy group, is reacted with methylene iodide in the presence of zinc, and any blocking groups present are split off, any hydroxy groups present in the 11- and/or 20-position are oxidized, or any free hydroxy groups present are esterified.

To conduct the process according to procedure (a), a conventional fermentation with an 11α- or 11β-hydroxylating microorganism is employed. For 11α-hydroxylation, fungal strains of the genus Aspergillus (e.g., *Aspergillus ochraceus*) are preferably employed as the microorganisms. For 11β-hydroxylation, fungal strains can be used, for example, of the genera Curvularia (for example, *Curvularia lunata*), Cunninghamella (e.g., *Cunninghamella bainieri*, *Cunninghamella elegans*, *Cunninghamella echinolata*, and *Cunninghamella blackesleana*), Absidia (e.g., *Absidia orchidis* and *Absidia coerula*), Helmintosporium, Rhizoctonia (e.g., *Rhizoctonia solani*), Verticillium (e.g., *Verticillium theobromae*), Stachylidium (e.g., *Stachylidium bicolor*), Pellicularia (e.g., *Pellicularia filamentosa*), or Colletotrichum (e.g., *Colletotrichum pisi*). The fermentation with these microorganisms is conducted under the usual conditions. During this reaction, any ester group in the 21-position is split off in most cases to give the free 21-hydroxy group. The process is preferably conducted with those compounds of general Formula II bearing a hydroxy group or an acyloxy group in the 21-position.

the dehydrogenation of the steroids of general Formula I saturated in the 1,2-position, employing an optional subsequent reaction, can be accomplished either microbiologically or chemically. For example, the Δ⁴-steroids can be dehydrogenated in the 1,2-position under the usual conditions with bacterical cultures of the genera Bacillus (e.g., *Bacillus lentus* or *Bacillus sphaericus*) or Arthrobacter (e.g., *Arthrobacter simples*) to give Δ¹,⁴-steroids. It is likewise possible to conduct the Δ¹-dehydrogenation by heating the Δ⁴-steroids with an oxidizing agent conventionally employed for this reaction, e.g., selenium dioxide or 2,3-dichloro-5,6-dicyanobenzoquinone, in an inert solvent.

The process of this invention according to variant (b) can be conducted under the conditions conventionally employed when introducing methylene groups into steroids by the Simmons-Smith reaction. (See John Friend, Organic Reactions in Steroid Chemistry, vol. II, pp. 107–113, van Nostrand-Reinhold Co. New York et al., 1972.) An example is the reaction of compounds of general Formula II with methyl iodide in the presence of an ether (such as diethyl ether, diisopropyl ether, di-n-butyl ether, tetrahydrofuran, or 1,2-dimethoxyethane) and a zinc-copper or zinc-silver powder. Starting compounds of general Formula II for this reaction are those which have free, esterified, or etherified hydroxy groups and/or free or ketalized oxo groups. Preferred esterified hydroxy groups are alkanoyloxy groups of 1–8 carbon atoms, (e.g., formyloxy, acetoxy, the butyryloxy and trimethylacetoxy group) and benzoyloxy. Suitable etherified hydroxy groups are preferably groups which can readily be split, for example, the tert.-butoxy, benzyloxy and trimethylsilyloxy. Examples of suitable ketalized oxo groups are alkylenedioxy of 2–6 carbon atoms and 2—3 carbon atoms between the oxy groups, e.g., ethylenedioxy and 2,2-dimethyl-propylenedioxy.

After the reaction is completed, any ester, ether and/or ketal groups present can be conventionally split, for example, by hydrolyzing an trimethylsilyloxy, tert.-butoxy groups or alkylenedioxy groups present employing an acidic catalyst (such as hydrochloric acid, sulfuric acid, perchloric acid, or p-toluenesulfonic acid) in an aqueous lower alcohol or ketone or, respectively, in a water-containing polar ether (such as dioxane or tetrahydrofuran).

The optional subsequent oxidation of the 11β-hydroxy steroids of general Formula I to the corresponding 11-ketones, also is conducted employing conventional methods, e.g., with chromic acid, N-bromosuccinimide or N-bromoacetamide.

The optional subsequent saponification of esters also is conducted according to known methods. An example is the saponification of the esters in water or aqueous alcohols in the presence of an acidic catalyst, such as hydrochloric acid, sulfuric acid or p-toluenesulfonic acid, or a basic catalyst, e.g., potassium bicarbonate, potassium carbonate, sodium hydroxide or potassium hydroxide.

An optionally subsequent esterification of free hydroxy groups likewise is conducted according to conventional methods. Thus, for example, the hydroxy steroids can be esterified with acyl chlorides or acyl anhydrides in the presence of an acid, e.g., hydrogen chloride, p-toluenesulfonic acid or trifluoroacetic acid, or in the presence of a base, such as potassium carbonate, pyridine, collidine or p-dimethylaminopyridine.

It is also possible to esterify the hydroxy compounds with carboxylic acids in the presence of trifluoroacetic anhydride.

The salts of the 21-monosulfuric acid esters can be prepared from the 21-hydroxy compounds of general Formula I in a conventional manner, for example, by reacting the 21-hydroxy compounds with sulfur trioxide in pyridine and converting the thus-obtained sulfuric acid ester into an alkali salt, e.g., sodium or potassium salt, by treatment with an alkali base. It is also possible to produce the alkali salts of the 21-monophosphoric acid esters from the 21-hydroxy groups of general Formula I in a conventional manner. For example, by esterifying the 21-hydroxy compounds with sulfonic acid chloride in the 21-position; converting the 21-sulfonates into the 21-iodo compounds with alkali iodide in acetone; reacting the 21-iodo compounds with phosphoric acid in the presence of an organic base; and converting the thus-obtained phosphoric acid monoesters with alkali into the dialkali metal salts.

The novel corticoids of general Formula I are pharmacologically active compounds which are especially distinguished by pronounced anti-inflammatory activity upon topical administration. These compounds are often distinguished by a rapid onset of activity, a high level of activity and a long duration of activity. They possess a favorable resorbability and a relatively good stability in galenic preparations. The onset of activity and the duration of effectiveness of the novel methylene steroids, as well as their solubility in physiologically compatible solvents are, as in case of the conventional corticoids, primarily dependent on whether, and, if so, with which acid, a hydroxy group in the 11,17- and/or 21-position is esterified.

The novel compounds are suitable, in combination with the vehicles customary in galenic pharmacy, for the local treatment of contact dermatitis, eczema of a great variety of types, neurodermatoses, derythrodermia, burns, pruritus vulvae et ani, rosacea, erythematodes cutaneus, psoriasis, lichen ruber planus et verrucosus, and similar skin diseases.

Pharmaceutical compositions are produced in the usual manner by converting the effective agents, together with suitable additives, including a physiologically acceptable carrier adapted for topical application, such as, for example, solutions, lotions, ointments, creams, or plasters. In the thus-formulated medicinal agents, the concentration of active compound is dependent on the form of administration. In case of lotions and ointments, an active agent concentration of 0.001% to 2% is preferably employed.

Moreover, the novel compounds, optionally in combination with the customary vehicles and auxiliary agents, are also suitable for the preparation of inhalants.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1 a. 30 g. of 11$\beta$-hydroxy-1,4,16-pregnatriene-3,20-dione is combined in 300 ml. of absolute pyridine with 30 ml. of trimethylchlorosilane and agitated for 24 hours at room temperature. The mixture is then stirred into ice water, the thus-precipitated sediment is vacuum-filtered, washed out with water, and taken up in methylene chloride. After evaporation, 36.5 g. of crude 11$\beta$-trimethylsilyloxy-1,4,16-pregnatriene-3,20-dione is obtained. A sample recrystallized from diisopropyl ether melts at 196°–197.5° C.

b. 6.72 g. of potassium tert.-butylate is dissolved in 79 ml. of dimethylformamide and 13.2 ml. of tert.-butanol. The solution, cooled to −25° C., is combined with 5.3 ml. of trimethyl phosphite, and dry oxygen is passed through the mixture. Then, 8.8 g. of 11$\beta$-trimethylsilyloxy-1,4,16-pregnatriene-3,20-dione, dissolved in 62 ml. of absolute tetrahydrofuran, is added dropwise thereto, oxygen is passed through the mixture for 15 minutes, and the mixture is agitated for another 30 minutes at −25° C. After stirring into weakly acetic ice water, the thus-formed precipitate is filtered off, washed with water, taken up in methylene chloride, and dried. The residue is chromatographed on silica gel, and recrystallization from diisopropyl ether/methylene chloride yields 1.95 g. of 17-hydroxy-11$\beta$-trimethylsilyloxy-1,4,15-pregnatriene-3,20-dione, m.p. 193°–195.5° C.

c. 1.5 g. of 17-hydroxy-11$\beta$-trimethylsilyloxy-1,4,15-pregnatriene-3,20-dione is combined in 35 ml. of absolute tetrahydrofuran with 1.35 g. of lithium tri-tert.-butoxyalanate and agitated for 30 minutes at room temperature. The mixture is then stirred into ice water, acidified with dilute sulfuric acid, and extracted with methylene chloride. The organic phase is washed neutral with water, dried, and evaporated. The residue is chromatographed on silica gel, thus obtaining 1.17 g. of 17,20$\xi$-dihydroxy-11$\beta$-trimethylsilyloxy-1,4,15-pregnatrien-3-one as an oil.

d. 3.8 of 17,20$\xi$-dihydroxy-11$\beta$-trimethylsilyloxy-1,4,15-pregnatrien-3-one is dissolved in 25 ml. of absolute ether and 25 ml. of absolute 1,2-dimethoxyethane, combined with 7.6 g. of zinc-copper pair and 6.13 ml. of methylene iodide, and refluxed for 7.5 hours. Then, the same amount of Zn-Cu powder and methylene iodide is once again added, and the mixture is refluxed for another 18 hours. The reaction solution is then diluted with methylene chloride, and washed with saturated ammonium chloride solution and with water. After evaporation, the residue is chromatographed on silica gel, obtaining 2.5 g. of 17,20$\xi$-dihydroxy-11$\beta$-trimethylsilyloxy-15$\alpha$,16$\alpha$-methylene-1,4-pregnadien-3-one as an oil.

e. 2.5 g. of 17,20ξ-dihydroxy-11β-trimethylsilyloxy-15α,16α-methylene-1,4-pregnadien-3-one is dissolved in 73.5 ml. of dimethyl sulfoxide, cooled to 10°–15° C., 6.74 ml. of triethylamine is added thereto, and within 25 minutes a solution of 4.9 g. of pyridine — SO₃ complex in 19.5 ml. of dimethyl sulfoxide is added dropwise thereto. The mixture is then stirred for one hour at room temperature, added to ice water under agitation, and the thus-obtained precipitate is filtered off and taken up in methylene chloride. After drying and evaporation, the residue is chromatographed on silica gel, thus obtaining 2.0 g. of 17-hydroxy-11β-trimethylsilyloxy-15α,16α-methylene-1,4-pregnadiene-3,20-dione. A sample recrystallized from diisopropyl ether/methylene chloride melts at 216°–218.5° C.

f. 2.0 g. of 17-hydroxy-11β-trimethylsilyloxy-15α,16α-methylene-1,4-pregnadiene-3,20-dione is stirred in 40 ml. of methanol with 2 ml. of 1 + 1 diluted hydrochloric acid for 1.5 hours at room temperature. The mixture is then stirred into ice water, the thus-formed precipitate is vacuum-filtered, washed with water, and taken up in methylene chloride.

After drying and evaporation, the residue is recrystallized from ethyl acetate, thus obtaining 1.03 g. of 11β,17-dihydroxy-15α,16α-methylene-1,4-pregnadiene-3,20-dione, m.p. 233°–248° C. (decomposition).

EXAMPLE 2 a. 11.0 g. of 3β-acetoxy-15α,16α-methylene-5-pregnene-17,20ξ-diol is dissolved in 230 ml. of dimethyl sulfoxide, cooled to 15° C., and 30.8 ml. of triethylamine is added thereto. Within 30 minutes, a solution of 22 g. of pyridine — sulfur (VI) oxide complex in 100 ml. of dimethyl sulfoxide is added dropwise to he reaction mixture, and the latter is stirred for one hour at room temperature. Then, the mixture is stirred into weakly acetic ice water; the thus-produced precipitate is filtered off, washed thoroughly, and taken up in methylene chloride. After drying and evaporation, the residue is recrystallized from ethyl acetate, yielding 7.5 g. of 17-hydroxy-3β-acetoxy-15α,16α-methylene-5-pregnen-20-one, m.p. 245°–247° C. (decomposition).

b. 10.0 g. of 17-hydroxy-3β-acetoxy-15α,16α-methylene-5-pregnen-20-one is dissolved in part in 350 ml. of acetic acid and 100 ml. of chloroform, and 0.1 ml. of hydrogen bromide in acetic acid (37%) is added thereto. Within 1.5 hours, a solution of 2.85 ml. of bromine in 100 ml. of acetic acid is added dropwise thereto. The mixture is then agitated for 1 hour, the reaction solution is diluted with methylene chloride, washed with water, sodium bicarbonate solution, and water, and dried. Evaporation yields 17.9 g. of crude 5,6β,21-tribromo-17-hydroxy-3β-acetoxy-15α,16α-methylene-5α-pregnan-20-one.

c. 17.9 g. of crude 5,6β,21-tribromo-17-hydroxy-3β-acetoxy-15α,16α-methylene-5α-pregnan-20-one is heated under reflux and agitation for 4 hours in 400 ml. of acetone with 9.1 g. of sodium iodide and 40 g. of potassium acetate. After precipitation into ice water, the filtered-off precipitate is taken up in methylene chloride, dried, and evaporated. The residue is chromatographed on silica gel, and recrystallization from diisopropyl ether/acetone produces 4.75 g. of 17-hydroxy-3β,21-diacetoxy-15α,16α-methylene-5-pregnen-20-one, m.p. 197.5°–199° C.

d. A glass fermentor having a capacity of 20 liters is filled with 15 liters of a nutrient solution consisting of 0.3% yeast extract, 0.5% corn steep liquor, and 0.2% glucose. The solution is sterilized by heating for ½ hour to 120° C. and, after cooling, inoculated with 250 ml. of a 2-day shaker flask culture of Flavobacterium dehydrogenans (ATCC 13930). (The shaker flask culture is prepared by inoculating 250 ml. of the same medium with the supernatant broth of a 7 day-old tilted agar culture). After a growth of 24 hours at 30° C. under agitation (220 r.p.m.) and aeration (15 liters per minute), 900 ml. of the thus-produced culture is withdrawn under sterile conditions and transferred into a fermentor of equal size containing 14 liters of the same medium. After 6 hours, the culture broth is reduced to 13 liters, combined with a sterile-filtered solution of 6.5 g. of 17-hydroxy-3β,21-diacetoxy-15α,16α-methylene-5-pregnen-20-one in 100 ml. of dimethylformamide, and fermented for another 13 hours under the same conditions.

After the fermentation is completed, the culture broth is extracted three times with respectively 6 liters of methyl isobutyl ketone. The combined extracts are evaporated to dryness under vacuum. The residue is washed free of the defrother used in this process, "Silicone SH," with the aid of 100 ml. of hot hexane, resulting in 4.7 g. of crude product which is recrystallized from ethyl acetate with a minor addition of carbon, thus obtaining 3.13 g. of 17,21-dihydroxy-15α,16α-methylene-4-pregnene-3,20dione (yield: 68% of theory), m.p. 225°–226° C.

EXAMPLE 3

A 20-liter glas fermentor is charged with 14 liters of a nutrient solution of 3% glucose, 1% corn steep liquor, 0.2% NaNO₃, 0.1% KH₂PO₄, 0.2% K₂HPO₄, 0.05% MgSO₄, 0.002% FeSO₄, and 0.05% KCl. The fermentor is then sterilized by heating for ½ hour to 120° C, and, after cooling, inoculated with 900 ml. of a 3 day-old shaker flask culture of Pellicularia filamentosa f. sp. sasakii, IFO 6675. (The shaker flask culture is prepared by inoculating 900 ml. of the same medium with a supernatant broth of a 7-day agar slant.)

After 12 hours of growth at 29° C. under the aforedescribed conditions, a sterile-filtered solution of 17,21-dihydroxy-15α,16α-methylene-4-pregnene-3,20-dione in 100 ml. of dimethylformamide is added thereto. After another 36 hours of fermentation, the culture broth is filtered over gauze. The mycelium residue is washed several times with water. The filtrate and the washing water are extracted with methyl isobutyl ketone and worked up as described in Example 2(d). The crude product is chromatographed on silica gel with a gradient system of hexane-acetone.

Recrystallization from ethyl acetate yields 1.2 g. of 11β,17,21-trihydroxy-15α,16α-methylene-4-pregnene-3,20-dione, m.p. 209°–210° C.

From the polar fractions and after recrystallization from diisopropyl ether/acetone, one obtains 22 mg. of 11α,17,21-trihydroxy-15α,16α-methylene-4-pregnene-3,20-dione, m.p. 214°–215° C.

EXAMPLE 4

A 2-liter Erlenmeyer flask is charged with 500 ml. of a nutrient solution consisting of 1.5% peptone, 1.2% corn steep liquor, and 0.2% MgSO₄, sterilized, and inoculated with the supernatant broth of a 3 day-old agar slant of Bacillus lentus (ATCC 13805). After 48 hours of incubation on a rotary shaker (165 r.p.m.) at 30° C., 50 ml. of the culture are withdrawn under sterile conditions, transferred into a 2-liter Erlenmeyer flask with 500 ml. of a sterile nutrien solution, consisting of 0.1% yeast extract, 0.5% corn steep liquor, and 0.05% glucose, and shaken for 24 hours. Ten 2-liter Erlenmeyer flasks, filled with respectively 500 ml. of the same medium, are each inoculated with 50 ml. of the thus-obtained subculture, then each of these flasks is charged, after 6 hours, with a solution of 100 mg. of 11$\beta$,17,21-trihydroxy-15$\alpha$,16$\alpha$-methylene-4-pregnene-3,20-dione in 4 ml. of dimethylformamide, and shaken for 24 hours at 30° C. and at 165 r.p.m. The culture broths are combined and extracted with methyl isobutyl ketone. After evaporation, the extracts yield 1.2 g. of a crude product which, when recrystallized from diisopropyl ether/acetone, yields 11$\beta$,17,21-trihydroxy-15$\alpha$,16$\alpha$-methylene-1,4-pregnadiene-3,20-dione, m.p. 205°–207° C.

EXAMPLE 5

A 2-liter Erlenmeyer flask with 500 ml. of a sterile nutrient solution, consisting of 1% corn steep liquor, 1.25% soybean meal, and 0.005% soybean oil, is inoculated with the supernatant broth of a 10 day-old agar slant of *Aspergillus ochraceus* (ATCC 1008) and incubated for 72 hours at 30° C. and 165 r.p.m. Seven 2-liter Erlenmeyer flasks, charged with respectively 500 ml. of the same medium, are inoculated each with 50 ml. of this culture and then combined, after 16 hours, with respectively 100 mg. of 17,21-dihydroxy-15$\alpha$,16$\alpha$-methylene-4-pregnene-3,20-dione in 4 ml. of dimethyl sulfoxide. After 21 hours of contact time, the combined culture broths are extracted with methyl isobutyl ketone without separation of the mycelium. The extracts yield, after evaporation, 992 mg. of a crude product which results, after recrystallization, in 331 mg. of 11$\alpha$,17,21-trihydroxy-15$\alpha$,16$\alpha$-methylene-4-pregnene-3,20-dione, m.p. 213°–215° C.

EXAMPLE 6

Under the conditions of Example 4, six 2-liter Erlenmeyer flasks are used to obtain, from 600 mg. of 11$\alpha$,17,21-trihydroxy-15$\alpha$,16$\alpha$-methylene-4-pregnene-3,20-dione, 680 mg. of crude dehydrogenation product by fermentation with *Bacillus lentus* (ATCC 13805). This product yields, after purification by way of preparative thin-layer chromatography on silica gel plates in the system chloroform/methanol 95 + 5, pure 11$\alpha$,17,21-trihydroxy-15$\alpha$,16$\alpha$-methylene-1,4-pregnadiene-3,20-dione, m.p. 225°–227° C.

EXAMPLE 7

Under the same conditions as in Example 4, the 1,2-dehydrogenation of 11$\alpha$,17,21-trihydroxy-15$\alpha$,16$\alpha$-methylene-4-pregnene-3,20-dione is attained with Corynebacterium simplex (ATCC 6946).

EXAMPLE 8

100 mg. of 11$\alpha$,17,21-trihydroxy-15$\alpha$,16$\alpha$-methylene-1,4-pregnadiene-3,20-dione is dissolved in 4 ml. of dimethylformamide and combined, under agitation, with 6 mg. of lead (II) acetate and 0.08 ml. of acetic anhydride. After stirring the reaction mixture at room temperature for 2 hours, the reaction solution is poured into water. The thus-formed precipitate is vacuum-filtered, dried, recrystallized from ethyl acetateisopropyl ether, thus obtaining 11$\alpha$,17-dihydroxy-21-acetoxy-15$\alpha$,16$\alpha$-methylene-1,4-pregnadiene-3,20-dione.

EXAMPLE 9

500 mg. of 11$\alpha$,17-dihydroxy-21-acetoxy-15$\alpha$,16$\alpha$-methylene-1,4-pregnadiene-3,20-dione is combined in 15 ml. of acetone at 10° C. with 0.4 ml. of chromosulfuric acid (prepared from 267 g. of chromic acid, 400 ml. of water, 230 ml. of concentrated sulfuric acid, the volume having been replenished to 1 liter). The mixture is further stirred for 15 minutes at 10° C. and precipitated into ice water. The precipitate is filtered off, taken up in methylene chloride, washed with water, and dried. After evaporation, the product is chromatographed on silica gel, thus obtaining 17-hydroxy-21-acetoxy-15$\alpha$,16$\alpha$-methylene-1,4-pregnadiene-3,11,20-trione.

EXAMPLE 10 a. 11.35 g. of 17-hydroxy-3$\beta$,21-diacetoxy-15$\alpha$,16$\alpha$-methylene-5-pregnen-20-one is combined in 170 ml. of methanol and 170 ml. of methylene chloride under ice cooling with a solution of 568 mg. of potassium hydroxide in 10 ml. of methanol. The mixture is agitated for 1.5 hours at the freezing temperature. Thereafter, the mixture is neutralized with acetic acid, the solution is extensively concentrated under vacuum and precipitated into ice water. The thus-formed precipitate is vacuum-filtered, washed, and dried. Chromatography on silica gel and trituration with diisopropyl ether yield 7.3 g. of 17,21-dihydroxy-3$\beta$-acetoxy-15$\alpha$,16$\alpha$-methylene-5-pregnen-20-one. A sample recrystallized from ethyl acetate melts at 228°–233.5° C. (decomposition).

b. 7.0 g. of 17,21-dihydroxy-3$\beta$-acetoxy-15$\alpha$,16$\alpha$-methylene-5-pregnen-20-one is agitated in 280 ml. of acetic acid with 700 mg. of zinc acetate containing water of crystallization for a period of 2 hours at 120° C. The mixture is then extensively concentrated under vacuum, the residue is taken up in methylene chloride and washed neutral with water. Evaporation yields 7.0 g. of crude 20-hydroxy-3$\beta$-acetoxy-15$\alpha$,16$\alpha$-methylene-5,17(20)-pregnadien-21-al.

c. 7.0 g. of 20-hydroxy-3$\beta$-acetoxy-15$\alpha$,16$\alpha$-methylene-5,17(20)-pregnadien-21-al is allowed to stand with 28 ml. of pyridine with 14 ml. of acetic anhydride for 1 hour at room temperature. The mixture is then stirred into ice water; the precipitate is filtered off and taken up in ether. The ether phase is washed with dilute hydrochloric acid, water, sodium bicarbonate solution, and water. After evaporation, the residue is chromatographed on silica gel, thus producing 6.5 g. of 3$\beta$,20-diacetoxy-15$\alpha$,16$\alpha$-methylene-5,17(20)-pregnadien-21-al. A sample recrystallized from diisopropyl ether melts at 147.5°–151° C.

d. 6.5 g. of 3$\beta$,20-diacetoxy-15$\alpha$,16$\alpha$-methylene-5,17(20)-pregnadien-21-al is mixed in 65 ml. of tetrahydrofuran with 6.5 g. of lithium tri-tert.-butoxyalanate and agitated for 30 minutes at room temperature. The mixture is then stirred into ice water, acidified with dilute sulfuric acid, and extracted with methylene chloride. After drying and evaporation, 6.5 g. of crude 21-hydroxy-3$\beta$,20-diacetoxy-15$\alpha$,16$\alpha$-methylene-5,17(20)-pregnadiene is obtained.

e. 6.5 g. of 21-hydroxy-3$\beta$,20-diacetoxy-15$\alpha$,16$\alpha$-methylene-5,17(20)-pregnadiene is refluxed in 260 ml. of methanol with 65 ml. of 2N hydrochloric acid for 3.5 hours. Thereafter, the mixture is precipitated into ice water, the precipitate is filtered off, taken up in methylene chloride, washed with water, and dried. The residue obtained after evaporation is chromatographed on silica gel. Recrystallization from ethyl acetate yields 2.6 g. of 3β,21-dihydroxy-15α,16α-methylene-5-pregnen-20-one, m.p. 174.5°– 179.5° C.

f. 2.0 g. of 3β,21-dihydroxy-15α,16α-methylene-5-pregnen-20-one is dissolved in 20 ml. of dimethylformamide and 2 ml. of acetic anhydride, combined with 1.28 g. of lead acetate, and stirred for 1.5 hours at room temperature. The mixture is then stirred into ice water, the thus-formed precipitate is vacuum-filtered, washed, and dried. Recrystallization from ethyl acetate produces 1.8 g. of 3β-hydroxy-21-acetoxy-15α,16α-methylene-5-pregnen-20-one, m.p. 168.5°– 169.5° C.

g. 500 mg. of 3β-hydroxy-21-acetoxy-15α,16α-methylene-5-pregnen-20-one is combined in 25 ml. of toluene and 1 ml. of cyclohexanone with a solution of 100 mg. of aluminum isopropylate in 2 ml. of toluene and heated for 45 minutes while conducting a gradual distillation. The mixture is then diluted with ether, and washed with dilute sulfuric acid and water. After dying and evaporation, the mixture is chromatographed on silica gel, and recrystallization from diisopropyl ether yields 275 mg. of 21-acetoxy-15α,16α-methylene-4-pregnene-3,20-dione, m.p. 124–125° C.

EXAMPLE 11

A glass fermentor having a capacity of 20 liters is charged with 15 liters of a nutrient solution of 4.4% glucose (starch sugar), 1% malt extract, 0.3% NaNO$_3$, 0.1% KH$_2$PO$_4$, 0.05% KCl, 0.05% MgSO$_4$, 0.002% FeSO$_4$, and 0.5% corn steep liquor, sterilized by heating for ½ hour to 120° C., and inoculated after cooling with a 3 day shaker flask culture of Curvularia lunata (NRRL 2380). (The shaker flask culture is prepared by the inoculation of 250 ml. of the same medium with the supernatant broth of a 7 day-old agar plant.) After 48 hours of growth at 30° C. under agitation (220 r.p.m.) and aeration (15 liters per minute), 900 ml. of the thus-produced culture is withdrawn under sterile conditions and transferred into a fermentor of equal size with 14 liters of the same medium. After 12 hours, 3 g. of 21-acetoxy-15α,16α-methylene-4-pregnene-3,20-dione – dissolved in 100 ml. of dimethylformamide – is added thereto, and the mixture is fermented for another 28 hours. The mixture is worked up as described in Example 3, thus obtaining 2.7 g. of a crude product which is separated by column chromatography on silica gel, yielding 11β,21-dihydroxy-15α,16α-methylene-4-pregnene-3,20-dione.

EXAMPLE 12

Under the conditions of Example 4, 200 mg. of 11β,21-dihydroxy-15α,16α-methylene-4-pregnene-3,20-dione is dehydrogenated in two 2-liter Erlenmeyer flasks with Bacillus lentus (ATCC 13805) to obtain 11β,21-dihydroxy-15α,16α-methylene-1,4-pregnadiene-3,20-dione.

EXAMPLE 13 a. 2.5 ml of liquid hydrogen fluoride is added to 2.5 ml. of dimethylformamide cooled to −40° C. The reaction mixture is combined with 250 mg. of N-bromosuccinimide, and then 500 mg. of 3β-hydroxy-21-acetoxy-15α,16α-methylene-5-pregnen-20-one, dissolved in 5 ml. of methylene chloride, is introduced into this reaction mixture. The latter is agitated for 5 minutes at −15° C., poured into saturated potassium bicarbonate solution, and extracted with methylene chloride. After drying and evaporation, 700 mg. of crude 6β-fluoro-5-bromo-3β-hydroxy-21-acetoxy-15α,16α-methylene-5α-pregnan-20-one is obtained.

b. 700 mg. of 6β-fluoro-5-bromo-3β-hydroxy-21-acetoxy-15α,16α-methylene-5α-pregnan-20-one is combined in 15 ml. of acetone with 0.55 ml. of chromosulfuric acid (prepared from 267 g. of chromic acid, 400 ml. of water, 230 ml. of concentrated sulfuric acid, replenished to a volume of 1 liter) and stirred for 10 minutes at room temperature. The mixture is then stirred into ice water, the precipitate is filtered off, taken up in methylene chloride, and dried. Evaporation yields 700 mg. of crude 6β-fluoro-5-bromo-21-acetoxy-15α,16α-methylene-5α-pregnane-3,20-dione.

c. 700 mg. of 6β-fluoro-5-bromo-21-acetoxy-15α,16α-methylene-5α-pregnane-3,20-dione is stirred in 15 ml. of acetic acid for 3 hours at 30° C. Then, 300 mg. of crystalline sodium acetate is added and the mixture is stirred at 30° C. for another 10 minutes. Subsequently the mixture is stirred into ice water, the precipitate is filtered off, washed with water, and taken up in methylene chloride. After drying and evaporation, the residue is chromatographed on silica gel, and recrystallization from diisopropyl ether yields 150 mg. of 6α-fluoro-21-acetoxy-15α,16α-methylene-4-pregnene-3,20-dione, m.p. 155.5°– 157.5° C.

EXAMPLE 14

Under the conditions of Example 11, 3 g. of 6α-fluoro-21-acetoxy-15α,16α-methylene-4-pregnene-3,20-dione is fermented with Curvularia lunata (NRRL 2380) and worked up. The crude product (2.4 g.) is separated by column chromatography, resulting in 6α-fluoro-11β,21-dihydroxy-15α,16α-methylene-4-pregnene-3,20-dione.

EXAMPLE 15

Under the conditions of Example 4, 200 mg. of 6α-fluoro-11β,21-dihydroxy-15α,16α-methylene-4-pregnene-3,20-dione is dehydrogenated in two 2-liter Erlenmeyer flasks with Bascillus lentus (ATCC 13805) to obtain 6α-fluoro-11β,21-dihydroxy-15α,16α-methylene-1,4-pregnadiene-3,20-dione.

EXAMPLE 16 a. 500 mg. of 17-hydroxy-11β-trimethylsilyloxy-15α,16α-methylene-1,4-pregnadiene-3,20-dione is agitated in 50 ml. of acetic anhydride with 600 mg. of calcium carbonate for 40 hours at 140° C. The mixture is filtered off from the calcium carbonate, the filtrate is stirred into ice water, the thus-formed precipitate is vacuum-filtered, washed with water, and dried. Yield: 600 mg. of crude 17-acetoxy-11β-trimethylsilyloxy-15α,16α-methylene-1,4-pregnadiene-3,20-dione.

b. 600 mg. of crude 17-acetoxy-11β-trimethylsilyloxy-15α,16α-methylene-1,4-methylene-1,4-pregnadiene-3,20-dione is agitated in 15 ml. of methanol with 0.6 ml. of 1+1 diluted hydrochloric acid for 1.5 hours at room temperature. The mixture is then worked up as described in Example 1(e), and the residue is chromatographed on silica gel, yielding 240 mg. of 11β-hydroxy-17-acetoxy-15α,16α-methylene-1,4-pregnadiene-3,20-dione.

EXAMPLE 17

200 mg. of 11β,17,21-trihydroxy-15α,16α-methylene-4-pregnene-3,20-dione is allowed to stand in 1 ml. of pyridine with 0.5 l. of acetic anhydride for 18 hours at room temperature. The mixture is then stirred into ice water, the thusformed precipitate is vacuum-filtered, washed, and dried. Yield: 210 mg. of 11β,17-dihydroxy-21-15α,16α-methylene-4-pregnene-3,20-dione.

EXAMPLE 18

100 mg. of 11β,17,21-trihydroxy-15α,16α-methylene-4-pregnene-3,20-dione is allowed to stand in 1 ml. of pyridine with 0.5 ml. of butyric anhydride for 18 hours at room temperature. The mixture is then stirred into ice water, decanted off from the thus-separated oil, and the latter is taken up in methylene chloride. After preparative thin-layer chromatography, 115 mg. of 11β,17-dihydroxy-21-butyryloxy-15α,16α-methylene-4-pregnene-3,20-dione is obtained.

EXAMPLE 19

250 mg. of 11β,17,21-trihydroxy-15α,16α-methylene-1,4-pregnadiene-3,20-dione is allowed to stand in 1.5 ml. of pyridine with 0.75 ml. of caproic anhydride. The mixture is then worked up as described in Example 18 and purified, thus obtained 210 mg. of 11β,17-dihydroxy-21-hexanoyloxy-15α,16α-methylene-1,4-pregnadiene-3,20-dione.

EXAMPLE 20

250 mg. of 11β,21-dihydroxy-15α,16α-methylene-4-pregnene-3,20-dione is combined in 1.5 ml. of pyridine with 0.75 ml. of enanthic acid anhydride and allowed to stand for 18 hours at room temperature. The mixture is then reacted as described in Example 18 and worked up, thus obtaining 170 mg. of 11β-hydroxy-21-heptanoyloxy-15α,16α-methylene-4-pregnene-3,20-dione.

EXAMPLE 21

180 mg. of 11β,21-dihydroxy-15α,16α-methylene-1,4-pregnadiene-3,20-dione is reacted, as described in Example 17, with acetic anhydride in pyridine and worked up. Yield: 145 mg. of 11β-hydroxy-21-acetoxy-15α,16α-methylene-1,4-pregnadiene-3,20-dione.

EXAMPLE 22

200 mg. of 6α-fluoro-11β,21-dihydroxy-15α,16α-methylene-4-pregnene-3,20-dione is combined in 2 ml. of pyridine with 0.25 l. of pivalic acid chloride and allowed to stand for 18 hours at 5° C. The mixture is reacted and worked up as set forth in Example 18, thus obtaining 130 mg. of 6α-fluoro-11β-hydroxy-21-trimethylacetoxy-15α,16α-methylene-4-pregnene-3,20-dione.

EXAMPLE 23

200 mg. of 6α-fluoro-11β,21-dihydroxy-15α,16α-methylene-1,4-pregnadiene-3,20-dione is reacted, as disclosed in Example 18, with butyric anhydride in pyridine and worked up, yielding 150 mg. of 6α-fluoro-11β-hydroxy-21-butyryloxy-15α,-16α-methylene-1,4-pregnadiene-3,20-dione.

EXAMPLE 24

40 ml. of absolute pyridine is cooled to −15° C. and, under agitation, 2.59 ml. of freshly distilled sulfur trioxide is added dropwise thereto, so that the internal temperature does not rise above −5° C. Into this solution is introduced 20 g. of 6α-fluoro-11β,21-dihydroxy-15α,1-6α-methylene-1,4-pregnadiene-3,20-dione, and the mixture is rinsed with 10 ml. of pyridine. The reaction mixture is stirred at room temperature for 30 minutes, then diluted with 400 ml. of water, agitated for another 30 minutes, and adjusted to pH 8.5 with 70.5 ml. of 1N sodium hydroxide solution. To remove the pyridine, the mixture is extracted with methylene chloride. The pH of the aqueous phase is set to pH 8 with 1N sodium hydroxide solution, and the reaction solution is evaporated under vacuum at a bath temperature of 40° C. The residue is dissolved in 500 ml. of methanol, the sodium sulfate is filtered off, and the filtrate is evaporated under vacuum and dried, thus producing sodium (6α-fluoro-11β-hydroxy-3,20-dioxo-15α,16α-methylene-1,4-pregnadien-21-yl) sulfate.

EXAMPLE 25

Under cooling and agitation, 20 ml. of methanesulfonic acid chloride is added dropwise into a solution of 20 g. of 6α-fluoro-11β,21-dihydroxy-15α,16α-methylene-1,4-pregnadiene-3,20-dione in 200 ml. of pyridine. After a reaction time of 30 minutes, the reaction solution is poured into ice water, and the thus-precipitated 21-mesylate is filtered off. 15.4 g. of the thus-obtained 6α-fluoro-11β-hydroxy-21-mesyloxy-15α,16α-methylene-1,4-pregnadiene-3,20-dione is dissolved in 500 ml. of acetone and, after adding 15.4 g. of sodium iodide in 400 ml. of acetone, is heated to boiling for 15 minutes. The filtered reaction solution is evaporated under vacuum. The residue is agitated together with dilute sodium thiosulfate solution, vacuum-filtered, washed with water, dissolved in 300 ml. of acetone, and precipitated under heating with 120 ml. of water. After cooling, 14.1 g. of 6α-fluoro-21-iodo-11β-hydroxy-15α,16α-methylene-1,4-pregnadiene-3,20dione is isolated, having a decomposition point at 157°–160° C. 14.1 g. of the iodo compound is dissolved in 700 ml. of acetonitrile and refluxed with 14.1 ml. of orthophosphoric acid and 42 ml. of triethylamine for 3 hours. Thereafter, the reaction solution is concentrated under reduced pressure, the residue is taken up in methanol, and the solution is set to pH 11 with 1N methanolic sodium hydroxide solution. The residue is filtered off, the filtrate is evaporated under vacuum, and the rest is taken up in 70 ml. of methanol. The addition of ether causes the disodium salt to precipitate. The disodium salt can be purified by reprecipitation from methanol with ether, thus obtaining 11.9 g. of disodium-(6α-fluoro-11β-hydroxy-3,20-dioxo-15α,1-6α-methylene-1,4-pregnadien-21-yl)-phosphate.

EXAMPLE 26

Composition for an ointment 0.02% 6α-Fluoro-11β-hydroxy-21-butyryloxy-15α,1-6α-methylene-1,4-pregnadiene-3,20-dione
2.50% Allercurhexachlorophenate, micronized to a particle size of about 8 μ (Allercur registered trade mark for 1-p-chlorobenzyl-2-pyrrodidyl-methyl-benzimidazole)
6.00% Hostaphat KW 340 (R) (tert. ester of phosphoric acid and paraffin alcohol tetraglycolether)
0.10% sobic acid
10.00% neutral oil ("Migloyol 812")
3.50% stearyl alcohol
1.50% wool fat, anhydrous, DAB 6
75.90% desalted water

EXAMPLE 27

Composition for an inhalant 1.000 g 11β-Hydroxy-21-acetoxy-15α,16α-methylene-1,4-pregnadiene-3,20-dione (average particle size: smaller than 7 μ) and 39.00 g of ground lactose are mixed together. Respectively 40 mg of the mixture is filled into mating capsules. The inhalant can be applied, after opening the capsule, by inhaling, preferably sniffing, or a "Spinhaler" is used to administer the inhalant.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A methylene steroid of the formula

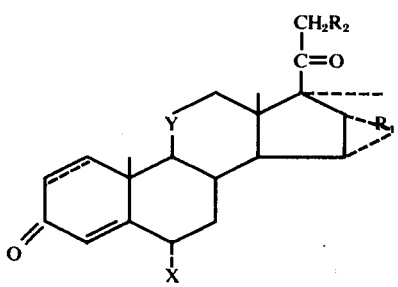

wherein X is H, F or $CH_3$, or a methyl group; Y is β-hydroxymethylene or carbonyl; one of $R_1$ and $R_2$ is a hydrogen atom and, when $R_2$ is a hydrogen atom, $R_1$ is hydroxy or alkanoyloxy of 1 to 8 carbon atoms and, when $R_1$ is a hydrogen atom, $R_2$ is hydroxy or acyloxy, wherein acyl is the acyl radical of sulfuric or phosphoric acid or a physiologically acceptable carboxylic acid of 1–12 carbon atoms.

2. A compound of claim 1 wherein $R_2$ is H.
3. A compound of claim 1 wherein $R_2$ is hydroxy.
4. A compound of claim 1 wherein $R_2$ is acetoxy.
5. A compound of claim 1 wherein Y is β-hydroxymethylene.
6. A compound of claim 1 wherein $R_1$ is hydroxy.
7. A compound of claim 1 wherein $R_1$ is a hydrogen atom.
8. 11β,17α-dihydroxy-15α,16α-methylene-1,4-pregnadiene-3,20-dione, a compound of claim 1.
9. 11β-Hydroxy-17α-acetoxy-15α,16α-methylene-1,4-pregnadiene-3,20-dione, a compound of claim 1.
10. 11β,21-Dihydroxy-15α,16α-methylene-4-pregnene-3,20-dione, a compound of claim 1.
11. 11β,21-Dihydroxy-15α,16α-methylene-1,4-pregnadiene-3,20-dione, a compound of claim 1.
12. 6α-Fluoro-11β,21-dihydroxy-15α,16α-methylene-4-pregnene-3,20-dione, a compound of claim 1.
13. 6α-Fluoro-11β,21-dihydroxy-15α,16α-methylene-1,4-pregnadiene-3,20-dione, a compound of claim 1.
14. 11β-Hydroxy-21-heptanoyloxy-15α,16α,-methylene-4-pregnene-3,20-dione, a compound of claim 1.
15. 11β-Hydroxy-21-acetoxy-15α,16α-methylene-1,4-pregnadiene-3,20-dione, a compound of claim 1.
16. 6α-Fluoro-11β-hydroxy-21-trimethylacetoxy-15α,16α-methylene-4-pregnene-3,20-dione, a compound of claim 1.
17. 6α-Fluoro-11β-hydroxy-21-butyryloxy-15α,16α-methylene-1,4-pregnadiene-3,20-dione, a compound of claim 1.
18. Sodium (6α-fluoro-11β-hydroxy-3,20-dioxo-15α,16α-methylene-1,4-pregnadien-21-yl) sulfate, a compound of claim 1.
19. Disodium-(6α-fluoro-11β-hydroxy-3,20-dioxo-15α,16α-methylene-1,4-pregnadien-21-yl)-phosphate, a compound of claim 1.
20. A pharmaceutical composition comprising an anti-inflammatorily effective concentration of at least one methylene steroid of claim 1 in admixture with a pharmaceutically acceptable carrier adapted for topical administration.
21. A method for the treatment of topical inflammations in mammals which comprises applying topically to the inflamed area an anti-inflammatorily effective amount of a compound of claim 1.
22. A compound of claim 1 wherein X is H.
23. A compound of claim 1 wherein X is F.
24. A compound of claim 1 wherein X is $CH_3$.

* * * * *

UNITED STATES PATENT AND TRADEMARK OFFICE
CERTIFICATE OF CORRECTION

PATENT NO. : 4,012,510
DATED : March 15, 1977
INVENTOR(S) : WIECHERT ET AL.

It is certified that error appears in the above–identified patent and that said Letters Patent are hereby corrected as shown below:

The formula in Claim 1 should read as follows:

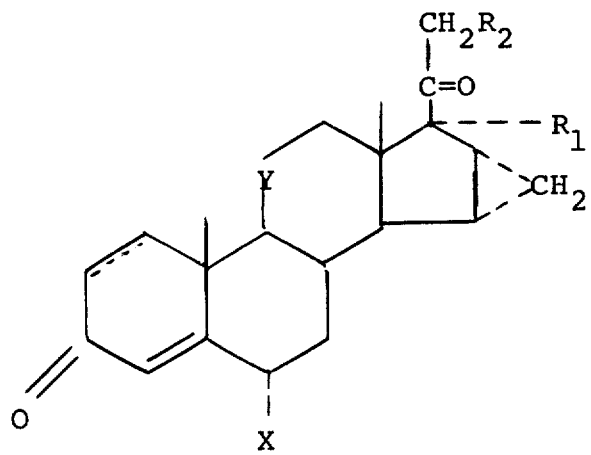

Signed and Sealed this

Seventeenth Day of May 1977

[SEAL]

Attest:

RUTH C. MASON
*Attesting Officer*

C. MARSHALL DANN
*Commissioner of Patents and Trademarks*